United States Patent
Chang et al.

(10) Patent No.: US 7,189,217 B2
(45) Date of Patent: Mar. 13, 2007

(54) SKIN PUNCTURE DEVICE WITH NEEDLE STICK PROTECTION

(76) Inventors: Joseph Jawshin Chang, 2207 NE. 13th Ave., Portland, OR (US) 97212; Eugene Yonchia Chang, 2207 NE. 13th Ave., Portland, OR (US) 97212; Victor Yonguor Chang, 7128 Staffordshire St., Houston, TX (US) 77030

( * ) Notice: Subject to any disclaimer, the term of this patent is extended or adjusted under 35 U.S.C. 154(b) by 0 days.

(21) Appl. No.: 11/352,830

(22) Filed: Feb. 13, 2006

(65) Prior Publication Data
US 2006/0189942 A1  Aug. 24, 2006

Related U.S. Application Data

(60) Provisional application No. 60/655,063, filed on Feb. 22, 2005.

(51) Int. Cl.
*A61M 5/178* (2006.01)
(52) U.S. Cl. .................. 604/164.08; 128/919
(58) Field of Classification Search .......... 604/110, 604/168.01, 164.08, 171, 187, 164, 167, 604/263, 264; 128/919
See application file for complete search history.

(56) References Cited

U.S. PATENT DOCUMENTS

| 5,000,740 | A | * | 3/1991 | Ducharme et al. ....... 604/162 |
| 5,120,319 | A | * | 6/1992 | Van Heugten et al. ... 604/168.01 |
| 5,201,713 | A | * | 4/1993 | Rossetti ............. 604/165.01 |
| 5,672,160 | A | * | 9/1997 | Osterlind et al. ........ 604/263 |
| 5,954,698 | A | * | 9/1999 | Pike ................... 604/167.03 |

* cited by examiner

*Primary Examiner*—Nick Lucchesi
*Assistant Examiner*—Christopher D. Koharski

(57) ABSTRACT

A skin puncture device for use as an intravenous catheter or blood collecting needle set is provided with a mechanism for protection against needle injury and access to fluid passageway during insertion. The assembly includes a flexible extension tube connected to the proximal end of the needle housing for use in difficult insertion sites. The extension tube provides access for fluid injection so that the passageway and needle can be filled with fluid prior to needle/catheter insertion, allowing diffusion of blood to provide evidence of successful venipuncture and allowing the infusion of small amounts of fluid into the vein to facilitate catheter advancement. The locking mechanism consists of two apertures in the needle housing and two pairs of needle guard locking tabs which selectively engage when the needle guard is pushed forward to its fully extended position upon completion of insertion or blood drawing, encapsulating the length of the needle.

14 Claims, 8 Drawing Sheets

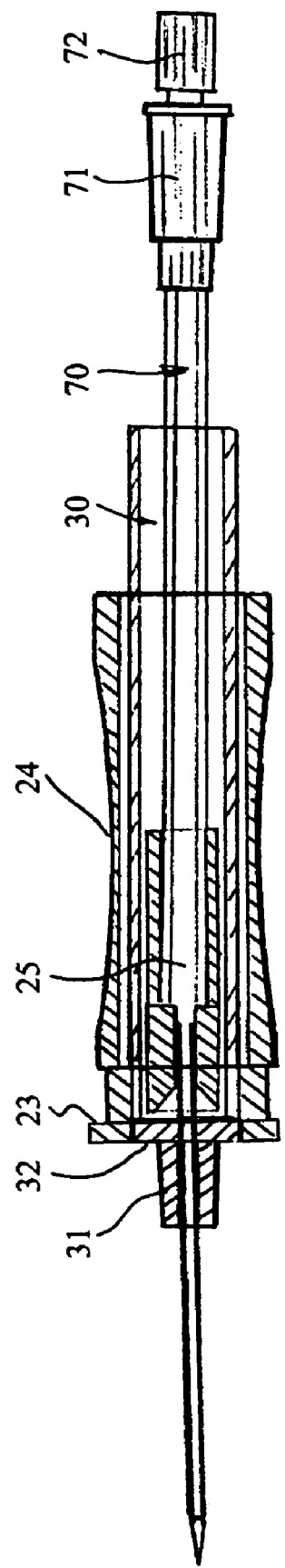
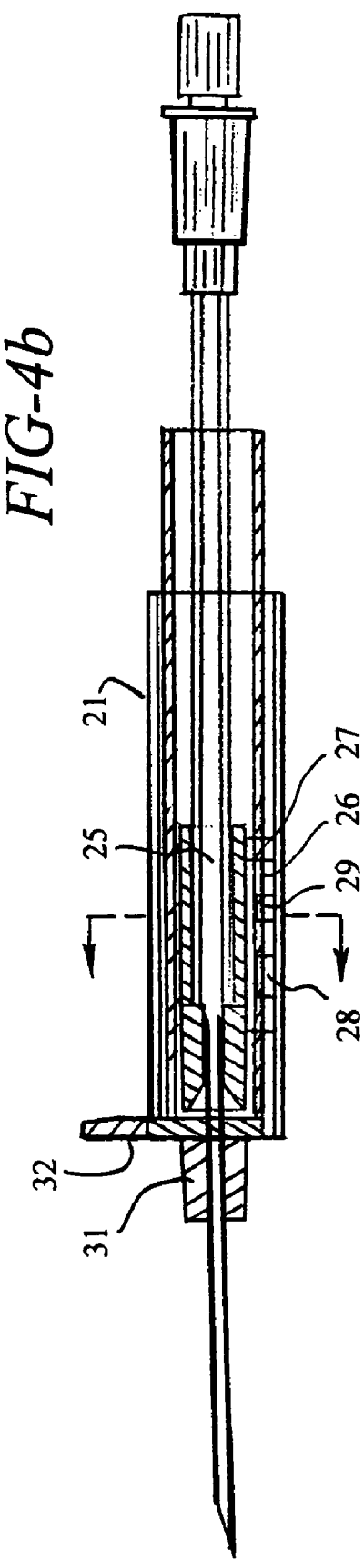
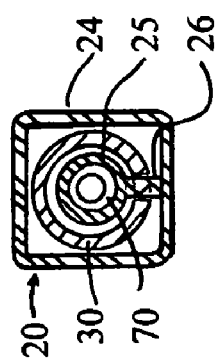
FIG-4a
FIG-4b
FIG-4c

SKIN PUNCTURE DEVICE WITH NEEDLE STICK PROTECTION

CROSS-REFERENCE TO RELATED APPLICATIONS

This nonprovisional application is a continuation of the prior-filed provisional application numbered 60/655,063 filed Feb. 22, 2005.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

This invention relates to a device for fluid administration as an intravascular (I.V.) catheter or for blood collection as a needle set with a safety system which shields the entire length of the bare needle after use to prevent accidental needle injury.

Intravenous needles for drawing blood or catheters for administration of fluid is one of the most common medical devices. A typical over-needle catheter requires the user to hold the device, insert it into a patient, withdraw needle from patient, and then dispose of the contaminated needle. Once the needle is withdrawn from the patient, the user's immediate priority is to press down the insertion site and to apply dressing. The withdrawn needle is usually placed aside conveniently and retrieved later. Since the needle at this time is blood contaminated, exposed in open environment, and located close to the user, accidental needle injuries could occur. Due to concerns that the user might be accidentally exposed to blood borne pathogens such as hepatitis and human immunodeficiency virus, there is an increasing need to protect the users from accidental needle injury.

An I.V. catheter device directed toward this need is shown in U.S. Pat. No. 5,000,740 and is currently commercially available as PROTECTIV IV Safety System. The catheter shown in this application includes a needle assembly in connection with a flash chamber located inside an open-top needle housing and a sliding tubular needle guard. Upon insertion of the catheter into a blood vessel, blood flows through internal space of the needle, and to the flash chamber of the needle housing. This signals successful venipuncture. By using the index finger to push a tab on the top of the needle guard while holding the needle housing with the thumb and middle finger, the user advances the catheter to a proper insertion depth and simultaneously retracts the needle from the catheter tube. As the needle is fully retracted inside the needle guard, a locking mechanism between the needle housing and the needle guard locks the two components and completely encapsulates the needle. The locked needle safety system may then be disposed of properly.

BRIEF SUMMARY OF THE INVENTION

While the I.V. catheter safety device described in U.S. Pat. No. 5,000,740 provides protection against accidental needle injury, it would be desirable to provide such a catheter in a smaller configuration with a fluid access feature that provides an alternate mechanism for obtaining blood flash back and a mechanism for collection of blood samples. The alternative flash back design provides a solution to a common problem while performing venipuncture; blood flash back may not occur when attempting insertion of a smaller catheter into the vein of a small patient or a patient with collapsed or sclerotic veins, because blood flow through such veins is limited, and flash back is further limited by the tiny bore of the small (e.g. 24 or 26 gauge) needles typically used for these patients. In this situation, the clinician may employ a unique technique for attempting the insertion. According to this technique, the clinician fills the needle and flash chamber internal space with saline prior to inserting the catheter into the blood vessel. With saline already present inside the needle, blood will diffuse through the fluid and appear in the clear flash chamber. Once the catheter and needle tip are verified to be inside the vein, the clinician may then infuse a small quantity of saline to dilate the vein, thus making further advancement of the catheter easier. In I.V. therapy, this technique is often referred to as "floating technique" for threading the catheter into a desired depth.

A major principle of the present invention is to incorporate a fluid access feature which enables to clinician to visualize the blood flash back through the mechanism of diffusion rather than conventional blood flow, to utilize the "floating technique," and to collect blood samples in the course of inserting the catheter. The present invention also provides an improved needle injury protection mechanism and a smaller needle housing and needle guard system, which allows for a smaller device that is easier to handle, especially for clinicians with smaller hands or for insertion in a difficult to reach site.

BRIEF DESCRIPTION OF THE SEVERAL VIEWS OF THE DRAWING

FIGS. 4a, 4b and 4c are the views for top, vertically longitudinal cross section, and vertically perpendicular cross-section of the needle housing and needle guard assembly of FIG. 3a without showing the catheter;

DETAILED DESCRIPTION OF THE INVENTION

Figures 1, 1A, 1B:
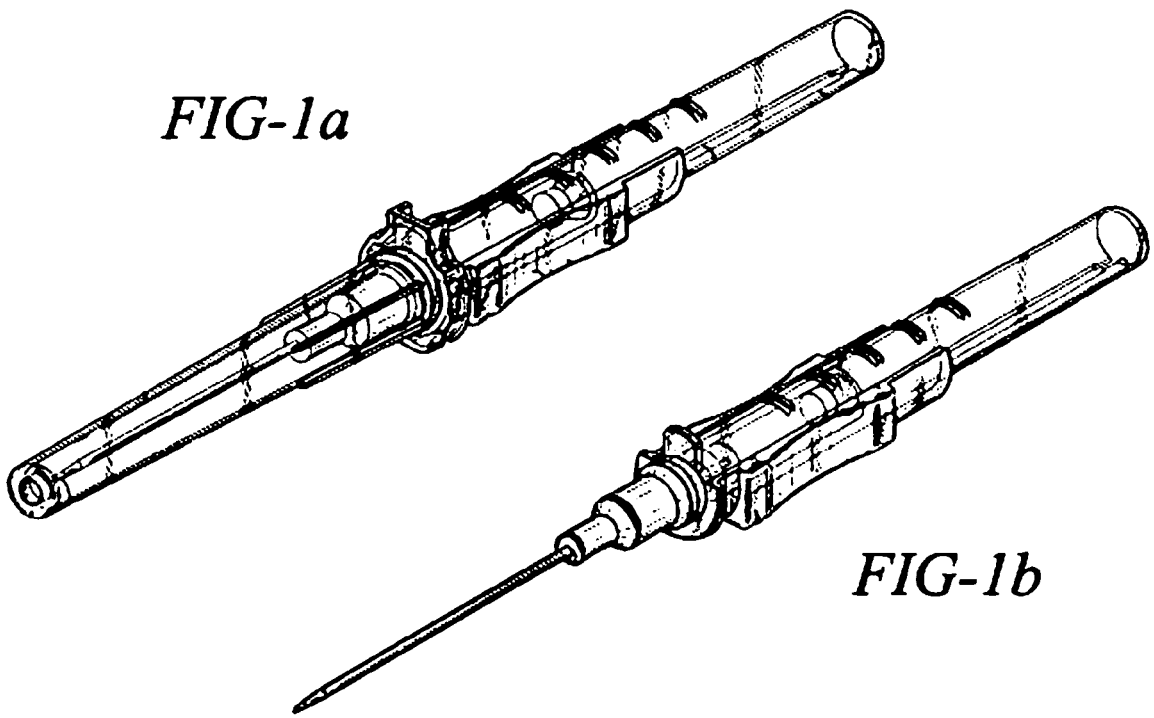
FIG. 1 is perspective view of the catheter assembly constructed in accordance with the principles of U.S. Pat. No. 5,000,740, representing a current commercially available safety catheter.
Figure 2:
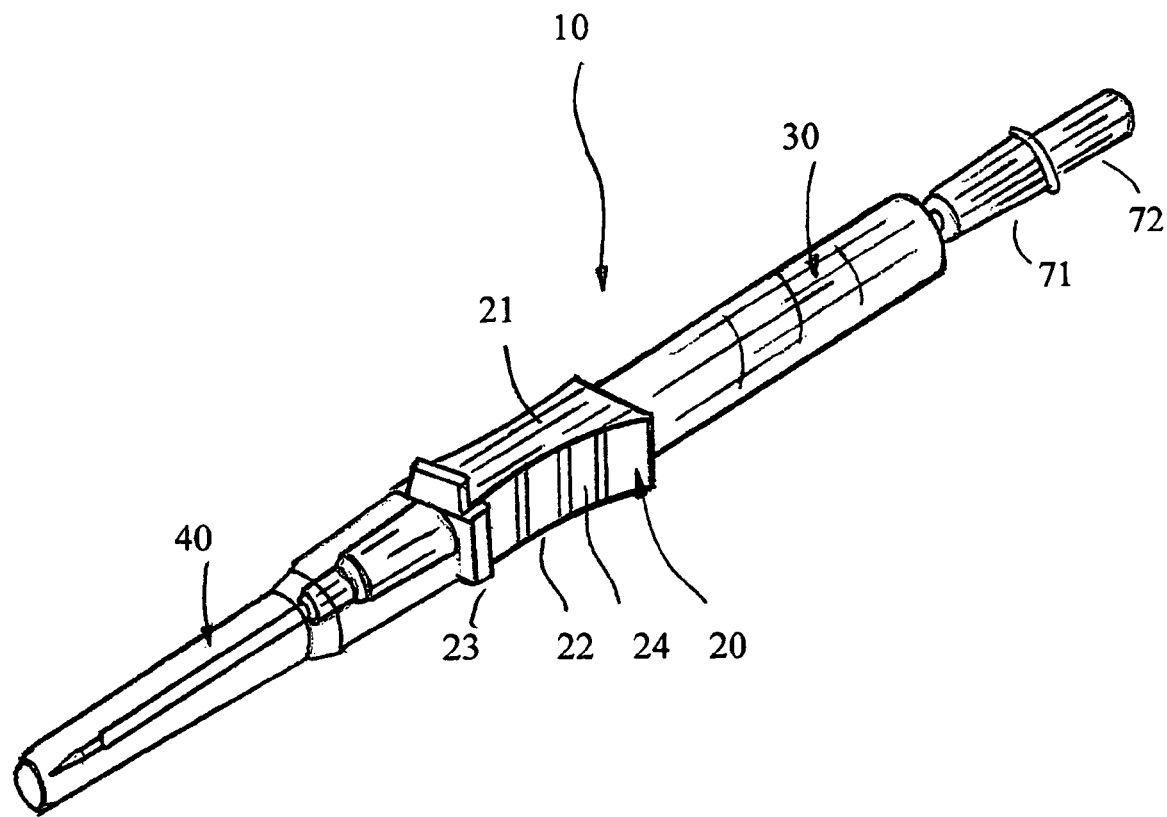
FIG. 2 is perspective view of the safety catheter assembly constructed in accordance with the principles of the present invention, indicating improvements over the device shown in FIG. 1.

Referring to FIG. 2, a catheter assembly 10 constructed in accordance with the principles of the present invention is shown. The assembly 10 includes a rectangular shaped needle housing 20 which has a closed top 21, a closed bottom 22, a pair of extending flanges 23 located at distal end of needle housing, and two contoured side walls 24 on both sides of needle housing for use as finger grips. Confined within the four walls of needle housing 20 is a needle guard 30 longitudinally moveable within the needle housing. Extending distally from the needle housing 20 is a protective sheath 40 which is removably attached to the needle housing flanges 23.

Figures 3A, 3B:
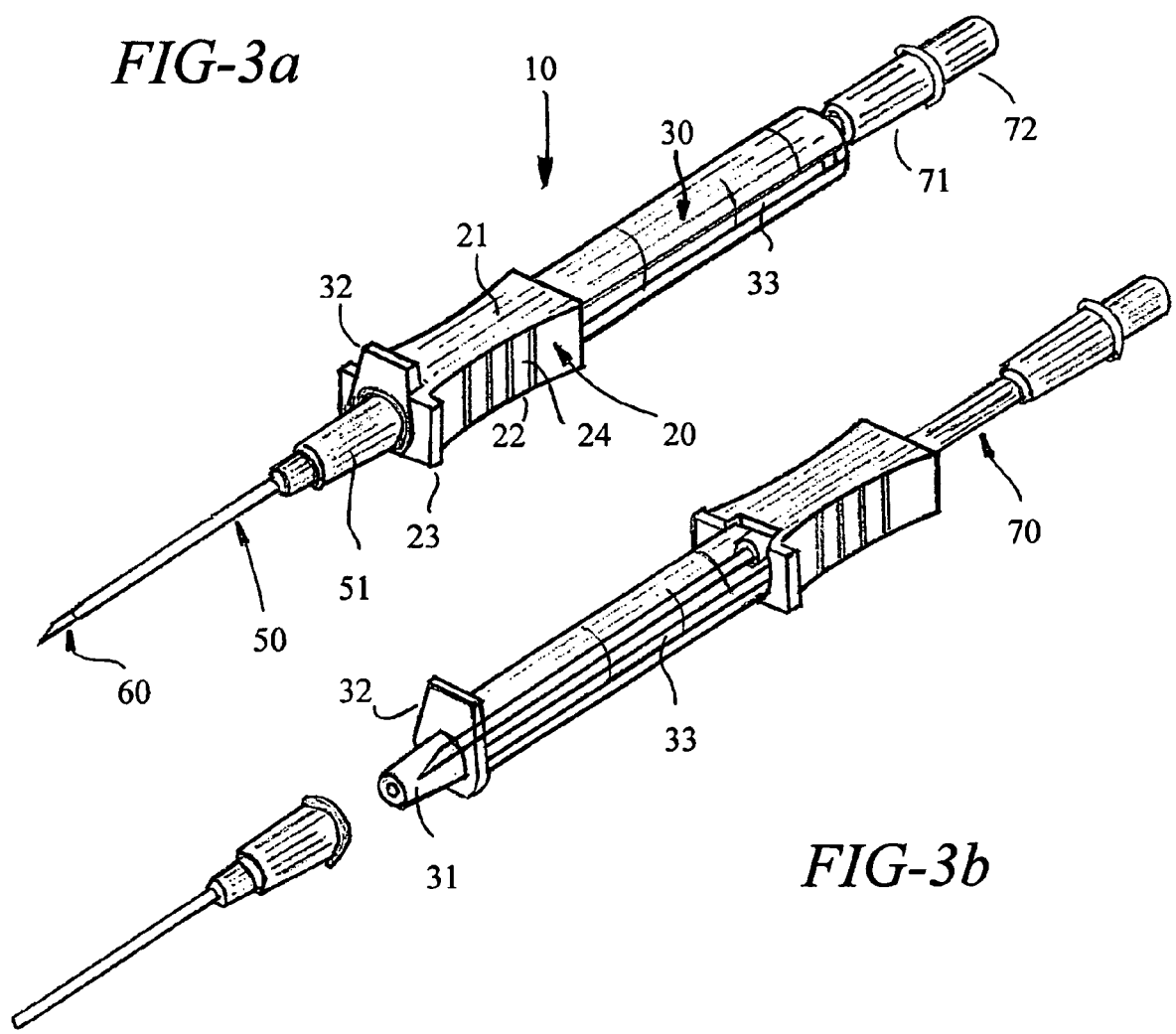
FIGS. 3a and 3b are perspective views of the catheter with the sheath removed and after the needle is retracted into the needle guard and locked in place. The catheter is left on the patient for subsequent IV administration procedures.

With the protective sheath 40 removed, FIG. 3a shows catheter 50 fitted over the needle 60. The sharp point of the needle 60 is seen to extend from the distal end of the catheter 50. The proximal end of the catheter 50 is attached to a conical fitting 51 and snuggly seated over a needle guard nose 31. The needle guard 30 has at its distal end a vertically protruding push-off tab 32. As shown in FIG. 3b, when the needle guard 30 is fully extended and locked in place with needle housing 20, the entire length of the needle 60 is encapsulated inside the needle guard 30.

The needle housing of a catheter assembly constructed in accordance with the principles of this invention for improved flash back capability is shown in FIGS. 4a, 4b, and 4c. At the top of needle housing 20 is a covered top plate 21. In order to make the entire needle guard and needle housing shown in FIG. 3b as small as possible, all plastic walls of needle housing 20 are kept as thin as possible. In this situation the covered top plate 21 is needed for keeping the two contoured side walls 24 from collapsing when clinician uses the two contoured sidewalls for finger griping during I.V. insertion. Centrally located within the needle housing is a connecting chamber 25 with needle 60 extends from the distal end of the connecting chamber and an extension tubing 70 with a conical fitting 71 and a porous end plug 72 is connected to proximal end of the connecting chamber. As illustrated in FIGS. 4b and 4c, the connecting chamber 25 shown in FIG. 4a is supported by a longitudinal base 26 having at its proximal end a wedge-shaped ramp 27 and with a plurality of rectangular apertures 28 and 29 located close to the distal end.

Figure 5A:
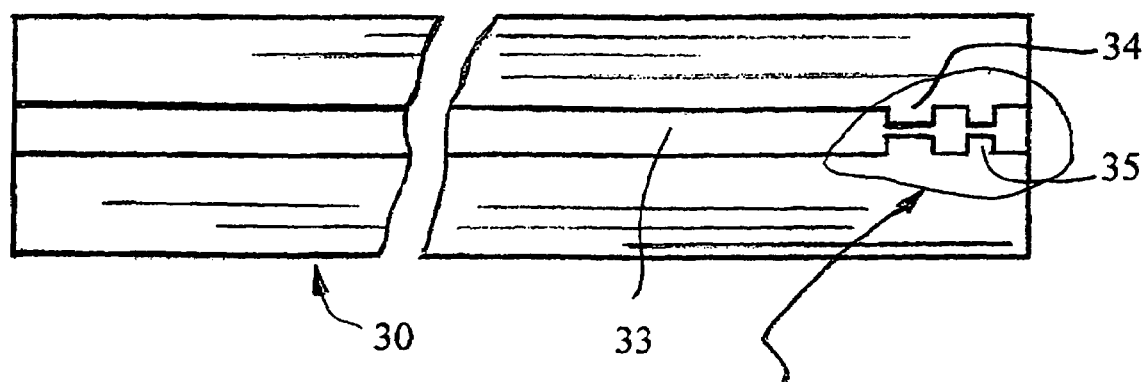
FIGS. 5a and 5b illustrate bottom views of the needle guard showing a longitudinal slot and two pairs of locking tabs.
Figure 5B:
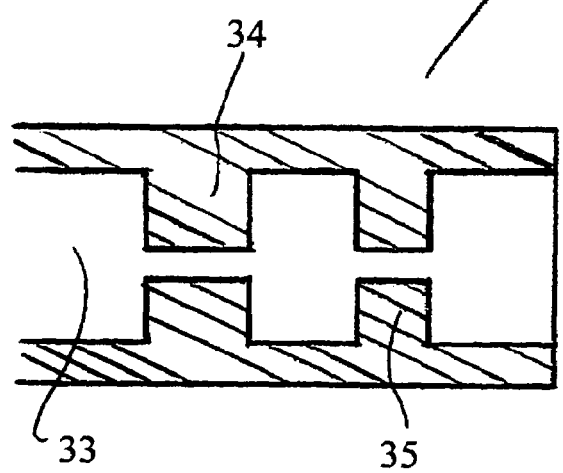
Figure 6A:
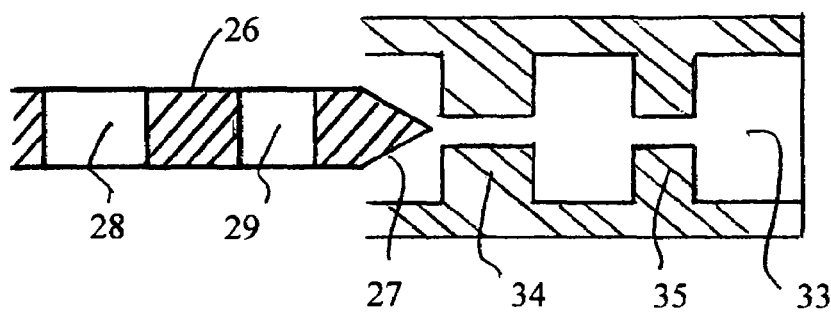
FIGS. 6a, 6b, and 6c describe sequence of double locking mechanism when needle guard locking tabs are approaching, partially over, and completely drop inside the two apertures of the needle housing.
Figure 6B:
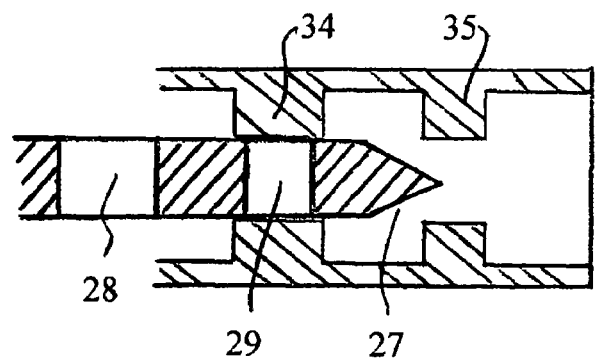
Figure 6C:
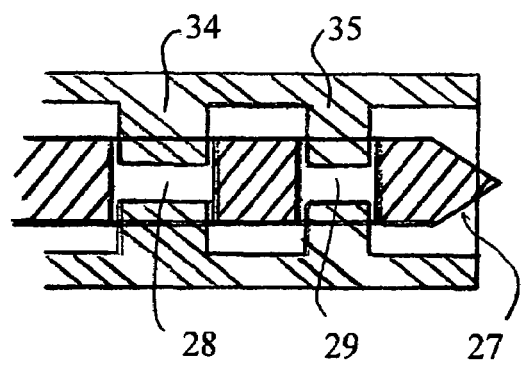

FIG. 5a is a bottom view of the needle guard 30 with a longitudinal slot 33 and two pairs of locking tabs 34 and 35 for interfacing with needle housing 20. The longitudinal slot 33 allows the needle guard 30 to slide inside needle housing 20 along the connecting chamber supporting base 26. FIG. 5b shows details of needle guard 30 having two pairs of radially protruded tabs 34 and 35 located at proximal end and at bottom of the needle guard 30. Said two pairs of locking tabs are of different widths with one pair having a width by at least one-tenth smaller than the other pair, and said two pairs of locking tabs are positioned no more than 40 mm apart. Wherein the said two apertures of said needle housing are spaced according to the distance of the two pairs of locking tabs, with the width of each aperture slightly larger than the widths of the mating tabs of the needle guard. As illustrated in FIGS. 6a, 6b, and 6c. the gap between each pair of tabs at unconstrained state is significantly narrower than the thickness of supporting base 26. Moreover, as an example, the width of tab 34 is dimensioned to be slightly smaller than aperture 28 but obviously larger than the width of aperture 29, and tab 35 is dimensioned slightly narrower than aperture 29. By pushing at push-off tab 32 while pulling needle housing 20 backward, the needle guard 30 slides forward and the two locking tabs, 34 and 35 are pushed open by wedge-shaped ramp 27 and continue to travel longitudinally along supporting base 26. Since tab 34 is wider than the width of aperture 29, tab 34 simply continues to move forward until it drops into aperture 28 and, simultaneously, tab 35 drops into aperture 29 to form a pair of locks. The double locking mechanism adds more strength and also enhanced resiliency of the locked needle housing 20 and needle guard 30 against bending in any direction. Under bending at one direction, one of the locking pair may become unlocked, such as tab 34 may be forced out of aperture 28. But this results in tab 35 becoming more securely engaged with aperture 29. Bending in an opposite direction would result in a similar effect. This provides assurance that at least one tab and aperture locking pair maintains securely locked if the locked assembly is subjected to bending.

The catheter assembly shown in FIG. 2 may be used in the conventional manner by removing the sheath 40, inserting the concentric catheter and needle through the skin of a patient into a blood vessel. When the point of needle 60 is in the blood stream, blood will flow through internal space of the needle and into the supporting chamber 25. This is commonly referred to as "blood flash back" for evidence of a successful venipuncture. However, when attempting insertion of a smaller catheter into the blood vessel of a small patient or patient with collapsed, sclerotic veins, blood flash back may not occur. The reason is that blood flow through the tiny bore of a small (e.g. 24 or 26 gauge) needle is rather limited. In this situation, prior to inserting the catheter into the blood vessel, the clinician can attach a syringe to the conical fitting 71 to fill the internal space of needle 60 and extension tubing 70 with saline. With saline already present in the fluid communicating pathway for performing insertion, blood can diffuse through saline and appear in the clear flash chamber or tubing to provide evidence of successful venipuncture. The clinician can then advance the catheter forward to a desired insertion depth. Again, for tiny blood vessel or patient with damaged, sclerotic vein, advancing a catheter could be difficult. In this case, the clinician can further infuse small amount of saline to dilate the blood vessel to facilitate catheter advancement. After proper insertion depth is achieved, the clinician can then use one hand to apply digital pressure to hold down the catheter and use the other hand to push against tab 31 while simultaneously pulling housing 20 backward until the entire length of needle 60 is retracted into needle guard 30 and the needle guard is securely locked with needle housing 20. The locked needle guard and needle housing assembly may then be detached from catheter conical fitting 51 and set aside for disposal without concern for accidental needle injury to the user or others.

Figure 7:
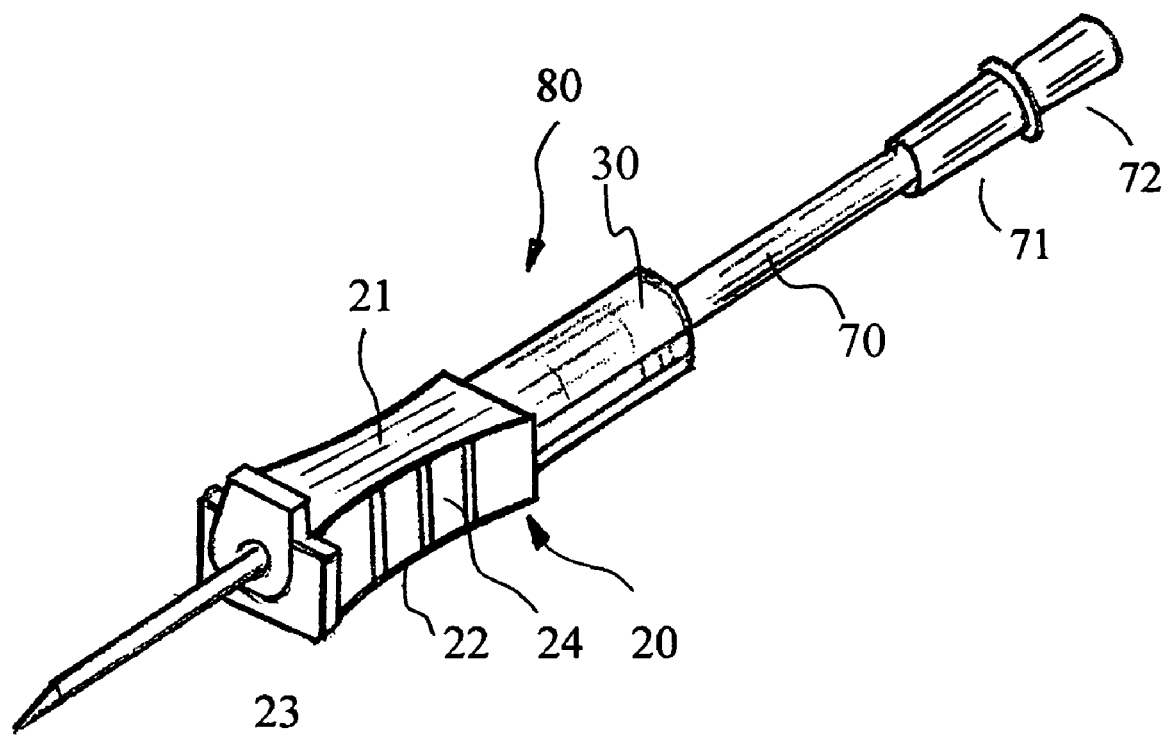
FIG. 7 is perspective view of a safety needle infusion or blood collection set assembly with sheath removed, constructed in accordance with the principles of the present invention.
Figure 8:
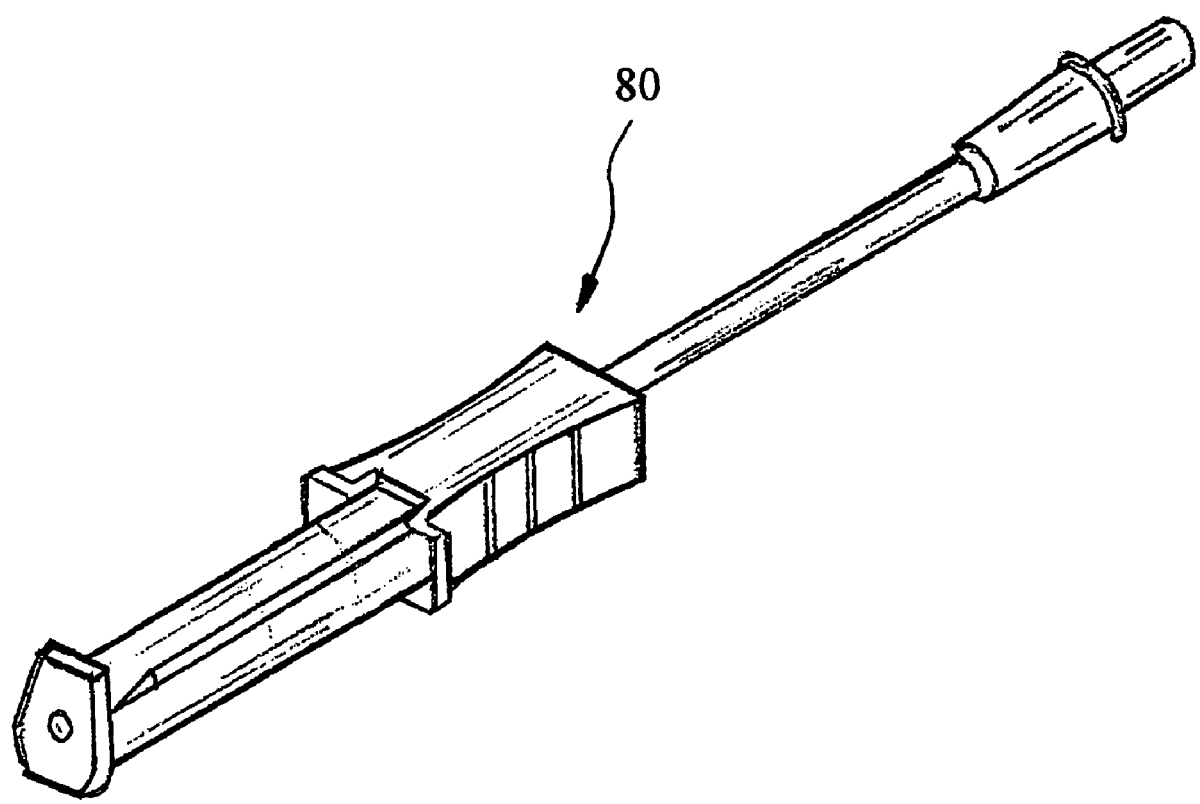
FIG. 8 is perspective view of the needle set device of FIG. 7, after the needle is retracted into the needle guard and locked in place.

The above descriptions for an I.V. catheter can be slightly modified for use as a blood collection needle set. The modification includes: deletion of catheter 50, conical fitting 51, and needle guard nose 31 from the assembly 10. As illustrated in FIG. 7, the assembly 80 includes a rectangular shaped needle housing 20 which has a closed top 21, a closed bottom 22, a pair of extending flanges 23 located at distal end of needle housing, and two contoured side walls 24 on both sides of needle housing for use as finger grips. Centrally located within the needle housing is a connecting chamber 25 with needle 60, which extends from the distal end of the chamber 25, and an extension tubing 70 with a conical fitting 71 and a porous end plug 72 connected to the proximal end of the connecting chamber 25. The connecting chamber has a supporting base 26 with a wedge 27 at its proximal end and a pair of apertures 28 and 29 located in close vicinity to the distal end. A tubular needle guard 30 located within the four walls of needle housing 20 has a bottom slot 33 for sliding longitudinally inside needle housing 20 along supporting base 26. Located at proximal end of needle guard 30 are two pairs of locking tabs 34 and 35 for engaging with two apertures 28 and 29 of needle housing 20. Needle guard 30 has at its distal end a vertically protruding push-off tab 32. When insertion and evidence of successful venipuncture is achieved through blood flash back and needle advancement mechanism described above, clinician can then use the same syringe for blood sampling or attach the conical fitting 71 to a commercially available holder, such as Vacutainer, for collecting blood into tubes. After blood sampling procedure is complete, clinician can then use a finger to push on tab 32 and simultaneously pull needle housing 20 backward with other fingers to retract and fully encapsulate needle 60 and to lock the needle guard 30 with needle housing 20. The locked needle guard and needle housing can then be set aside for disposal without concern for inadvertent needle injury.

What is claimed is:

1. A catheter assembly with access to fluid communication for insertion into a blood vessel and with a safety mechanism for protection against needle stick injury comprising:
    a clear rectangular needle housing, having a flat bottom, a flat top, and two contoured side walls,
    a clear tubular needle guard slidably located within said needle housing having a conical fitting at its distal end and a longitudinal bottom slot,
    a connecting chamber, located inside said needle housing and said needle guard, including a supporting base for securing said connecting chamber with said needle housing; said connecting chamber connected at its proximal end to a flexible tube which extends beyond the proximal end of said needle guard for attachment to a standard female conical fitting,
    a removable end plug attachable to said standard female conical fitting,
    a hollow needle, extending from the distal end of said connecting chamber for insertion into a patient,
    a catheter, for attachment over said needle having a standard female conical fitting at its proximal end, wherein the catheter is tightly in contact with said needle guard distal end,
    a double locking means, having two apertures located on the distal end of said supporting base of said needle housing,
    wherein said double locking means also comprises two pairs of locking tabs located on the proximal end and at the bottom of said needle guard,
    wherein said two pairs of locking tabs are of different widths with one pair having a width at least one-tenth smaller than the other pair, and said two pairs of locking tabs are positioned no more than 40 mm apart,
    wherein said first pair of locking tabs is located distally to said second pair of locking tabs, and wherein said first pair of locking tabs is larger in width when compared to the second pair of locking tabs located proximally to said first pair of locking tabs,
    wherein when said needle guard is in a fully extended position relative to the distal end of said needle housing, said two pairs of locking tabs selectively fall into and engage said two apertures.

2. The catheter assembly of claim 1, wherein said hollow needle extends from said connecting chamber, and the passageway of said hollow needle is in fluid communication with the interior of said connecting chamber, extension tube, and female conical fitting.

3. The catheter assembly of claim 1 wherein said end plug can be removed for connecting a syringe to said female conical fitting to provide a fluid passageway that is configured for infusing saline prior to or during venipuncture through skin and into a blood vessel; wherein evidence of a successful venipuncture is observed by blood diffusing into said clear connecting chamber, and up through said fluid communication passageway.

4. The catheter assembly of claim 3 wherein said fluid passageway is configured for aspiration of blood to further provide evidence of successful venipuncture, or infusion of saline to dilate blood vessel for ease of advancing an inserted catheter into the desired depth.

5. The catheter assembly of claim 1 wherein said needle guard has a push tab located in the vicinity of said needle guard distal end, wherein pushing on said push tab while simultaneously pulling back said needle housing, said needle retracts and becomes fully encapsulated within said needle guard.

6. The catheter assembly of claim 1, wherein said two apertures located inside said needle housing are spaced according to the distance between the two pairs of said locking tabs, and with the width of each aperture slightly larger than the widths of the mating locking tabs on said needle guard; wherein upon sliding said needle guard forward to its fully extended position with respect to said needle housing, said locking tabs spring into said apertures and prevents said needle guard from further movement either forwardly or backwardly and also providing additional anchoring against bending in the vertical and horizontal directions.

7. The catheter assembly of claim 1, further including a removable protective sheath which surrounds said needle and catheter during shipping and storage; wherein said needle sheath includes a proximal end and means of removably engaging said distal end of said needle housing, wherein said needle housing has a generally planar bottom to prevent rolling of the catheter assembly when placed on a flat surface.

8. A blood collecting needle assembly comprising:
    a clear rectangular needle housing, having a flat bottom, a flat top, and two contoured side walls,
    a clear tubular needle guard slidably located within said needle housing having a longitudinal bottom slot,
    a connecting chamber, located inside said needle housing and said needle guard, includes a base for securing said connecting chamber with said needle housing; said connecting chamber is connected at its proximal end to a flexible extension tube which extends beyond the proximal end of said needle guard for attaching to a standard female conical fitting,
    a removable end plug attachable to said standard female conical fitting,
    a hollow needle, extending from the distal end of said connecting chamber for inserting into a patient,
    a double locking means, having two apertures located on the distal end of said supporting base of said needle housing, wherein said double locking means comprises two pairs of locking tabs located on the proximal end and at the bottom of said needle guard, wherein said two pairs of locking tabs are of different widths with one pair having a width at least one-tenth smaller than the other pair, and said two pairs of locking tabs are positioned no more than 40 mm apart, wherein said first pair of locking tabs is located distally to said second pair of locking tabs, and wherein said first pair of locking tabs is larger in width when compared to the second pair of locking tabs located proximally to said first pair of locking tabs, wherein when said needle guard is in a fully extended position relative to the distal end of said needle housing, said two pairs of locking tabs selectively fall into and engage said two apertures.

9. The blood collecting needle assembly of claim 8, wherein said hollow needle extends from said connecting chamber, and the passageway of said hollow needle is in fluid communication with the interior of said connecting chamber, extension tube, and female conical fitting.

10. The blood collecting needle assembly of claim 8 wherein said end plug can be removed for connecting a syringe to said female conical fitting to provide a fluid passageway configured for infusing saline while performing venipuncture through skin and into a blood vessel, wherein evidence of successful venipuncture is provided by observing blood diffusing into said clear connecting chamber, and up through said fluid communication passageway inside clear tubing.

11. The needle assembly of claim 10 wherein said fluid passageway is configured for aspiration of blood to further provide evidence of successful venipuncture, or infusion of saline to dilate blood vessel for ease of advancing an inserted needle into the desired depth.

12. The needle assembly of claim 8 wherein said needle guard has a push tab located in the vicinity of said needle guard distal end; wherein, by pushing on said push tab while simultaneously pulling back said needle housing, said needle retracts and becomes fully encapsulated within said needle guard.

13. The needle assembly of claim 8, wherein the said two apertures located inside said needle housing are spaced according to the distance between the two pairs of said locking tabs, and with the width of each aperture slightly larger than the width of the mating locking tabs on said needle guard; wherein upon sliding said needle guard forward to its fully extended position with respect to said needle housing, said locking tabs spring into said apertures and prevents said needle guard from further movement either forwardly or backwardly and also providing additional anchoring against bending in the vertical or horizontal directions.

14. The blood collecting needle assembly of claim 8, further including a removable protective sheath which surrounds said needle during shipping and storage prior to use of said assembly; wherein said needle sheath includes at its proximal end a means of removably engaging said distal end of said needle housing and wherein said needle housing has a generally planar bottom to prevent rolling of the needle assembly when placed on a flat surface.

* * * * *